United States Patent
Wong

(10) Patent No.: US 9,873,611 B2
(45) Date of Patent: Jan. 23, 2018

(54) METHOD FOR THE PRODUCTION OF HYDROGEN GAS AND SYNGAS IN SEPARATE STREAMS

(71) Applicant: Real Time Engineering Pte Ltd, Singapore (SG)

(72) Inventor: Song Yeng Wong, Singapore (SG)

(73) Assignee: Real Time Engineering Pte Ltd, Singapore (SG)

( * ) Notice: Subject to any disclaimer, the term of this patent is extended or adjusted under 35 U.S.C. 154(b) by 0 days.

(21) Appl. No.: 14/647,227

(22) PCT Filed: Nov. 27, 2012

(86) PCT No.: PCT/SG2012/000445
§ 371 (c)(1),
(2) Date: May 26, 2015

(87) PCT Pub. No.: WO2014/084794
PCT Pub. Date: Jun. 5, 2014

(65) Prior Publication Data
US 2015/0298970 A1    Oct. 22, 2015

(51) Int. Cl.
*C07C 1/04* (2006.01)
*C10G 2/00* (2006.01)
(Continued)

(52) U.S. Cl.
CPC ............ *C01B 3/08* (2013.01); *B01J 38/60* (2013.01); *C07C 1/04* (2013.01); *C07C 1/043* (2013.01); *C07C 1/0425* (2013.01); *C07C 1/0435* (2013.01); *C10G 2/32* (2013.01); *C10G 2/332* (2013.01); *C10J 3/06* (2013.01); *C10J 3/18* (2013.01); *C10J 3/20* (2013.01); *C10J 3/26* (2013.01); *C10J 3/82* (2013.01);
(Continued)

(58) Field of Classification Search
CPC ......... Y02P 20/145; C10K 1/04; C10K 1/007; C01B 3/08; C10G 2/332; C10G 2/32; C10J 2300/1807; C10J 3/06; C10J 2300/0953; C10J 3/20; C10J 2300/1659; C10J 2300/0916; C10J 3/18; C10J 3/82; C10J 3/26; C10J 2300/0983; Y02E 60/36; Y02E 50/32
See application file for complete search history.

(56) References Cited

U.S. PATENT DOCUMENTS

| 6,133,328 | A | 10/2000 | Lightner |
| 2008/0086946 | A1* | 4/2008 | Weimer ............... B01J 19/127 48/89 |
| 2009/0246118 | A1 | 10/2009 | Drnevich et al. |

FOREIGN PATENT DOCUMENTS

| JP | 37008355 | | 8/1959 |
| JP | S5537422 | A | 3/1980 |
| WO | 2014084794 | A1 | 6/2014 |

OTHER PUBLICATIONS

Chaudhari, S. T. et al. Energy & Fuels 2003, 17, 1062-1067.*
(Continued)

*Primary Examiner* — Medhanit W Bahta
(74) *Attorney, Agent, or Firm* — Harness, Dickey & Pierce, P.L.C.

(57) ABSTRACT

Provided is a process for producing hydrogen gas in a separate stream from syngas. An assembly for producing hydrogen gas in a separate stream from syngas and a method of producing hydrogen are also provided.

7 Claims, 1 Drawing Sheet

(51) Int. Cl.
  *C01B 3/08* (2006.01)
  *C10G 3/00* (2006.01)
  *B01J 38/60* (2006.01)
  *C10J 3/18* (2006.01)
  *C10J 3/26* (2006.01)
  *C10J 3/82* (2006.01)
  *C10K 1/04* (2006.01)
  *C10K 1/00* (2006.01)
  *C10J 3/06* (2006.01)
  *C10J 3/20* (2006.01)

(52) U.S. Cl.
  CPC .............. *C10K 1/007* (2013.01); *C10K 1/04* (2013.01); *C10J 2300/0916* (2013.01); *C10J 2300/0953* (2013.01); *C10J 2300/0983* (2013.01); *C10J 2300/1238* (2013.01); *C10J 2300/1646* (2013.01); *C10J 2300/1659* (2013.01); *C10J 2300/1807* (2013.01); *Y02E 50/32* (2013.01); *Y02E 60/36* (2013.01); *Y02P 20/145* (2015.11)

(56) References Cited

OTHER PUBLICATIONS

Weimer, A. W. et al. "Development of a Solar-thermal ZnO/Zn Water-splitting Thermochemical Cycle" Apr. 2009, pp. 1-19.*
Wegner, K. et al. Int. J. Hydrogen Energy Apr. 22, 2005, pp. 55-61.*
Evdokimova, A. K. et al. "Direct conversion of zinc sulfate solution to zinc oxide" Sb. Nauchn. Tr., Gos. Nauchn.-Issled. Inst. Tsvetn. Metal. (1965), No. 23, 293-303; Abstract only.*
O'Leary, D. "Hydrogen" Copyright 2000, pp. 1-6.*
The International Search Report and International Search Opinion dated Jun. 10, 2013 in PCT/SG2012/000445 (published WO2014/084794).
The International Preliminary Report on Patentability and Written Opinion dated Jun. 2, 2015 in PCT/SG2012/000445 (published WO2014/084794).
Japanese Office Action issued in Japanese Application 2015-544038 (English Translation provided by Marks and Clerk Singapore LLP).

* cited by examiner

METHOD FOR THE PRODUCTION OF HYDROGEN GAS AND SYNGAS IN SEPARATE STREAMS

CROSS-REFERENCE TO RELATED APPLICATIONS

This application is a National Stage of International Application No. PCT/SG2012/000445, filed Nov. 27, 2012. The entire disclosure of the above application is incorporated herein by reference.

FIELD OF THE INVENTION

The present invention relates to a process and an assembly for producing hydrogen gas and syngas.

BACKGROUND OF THE INVENTION

Hydrogen molecules and atoms are used in many commercial and industrial applications. Generally, hydrogen may be used for upgrading petroleum feed stock to more useful products. In addition, hydrogen is used in many chemical reactions, such as reducing or synthesizing compounds. Particularly, hydrogen is used as a primary chemical reactant in the production of useful commercial products, such as cyclohexane, ammonia, and methanol. Moreover, hydrogen itself is quickly becoming a fuel of choice because it reduces green house emissions. Particularly, hydrogen can be used in fuel cells and other similar applications to produce a substantially clean source of electricity for powering industrial machines and automobiles.

Research pertaining to the production of hydrogen from biomass using various means of gasification has attracted much attention in recent years. A common problem encountered in this field of research is the difficulty in removing carbon monoxide from a hydrogen gas stream. This process can be time-consuming, expensive and is a major reason why the commercialized production of hydrogen, using such techniques, has not been successful.

A conventional method of producing hydrogen from water using zinc metal catalysis can be represented by the chemical equation, as shown below:

$$Zn + H_2O \rightarrow ZnO + H_2$$

However, in practice it is found that the production of hydrogen using this method has a relatively low yield. Typically only 18% of zinc is consumed even when the reaction is performed using superheated steam at 700° C. This occurs due to the rapid formation of a passivating layer of zinc oxide on the surface of the zinc particle thus preventing the zinc metal below from reacting with the superheated steam.

One method for overcoming the problem with passivating layer formation is to use nano zinc that is smaller in diameter than the thickness of the passivating zinc oxide layer. However the use of nano zinc is extremely expensive rendering the method less cost effective.

Due to the high costs, the difficulty in purification and the adverse environmental factors associated with hydrogen production there is a need for an improved method of producing hydrogen gas.

SUMMARY OF INVENTION

The present invention seeks to address at least one of the problems in the prior art. The process of the present invention provides a process which is cost effective and environmentally friendly while enabling production of hydrogen gas and syngas separately, thus avoiding the need of a further purification step which may be expensive.

In general terms the invention relates to a process and assembly of producing hydrogen gas and syngas in separate streams. The advantage of the process is that the need for a further purification step to separate the stream is not required, making the process more cost effective and environmentally friendly.

In a first particular expression of the invention, there is provided a process of providing hydrogen gas and syngas in separate streams according to claim 1. Embodiments may be implemented according to any one of claims 2 to 4.

In a second particular expression of the invention, there is provided an assembly for providing hydrogen gas and syngas in separate streams according claim 5.

In a third particular expression of the invention, there is provided a method according to claim 6. Embodiments may be implemented according to any one of claims 7 to 10.

BRIEF DESCRIPTION OF FIGURES

Example embodiments of the invention will now be described with reference to the accompanying FIGURE in which.

DETAILED DESCRIPTION

Figure 1:
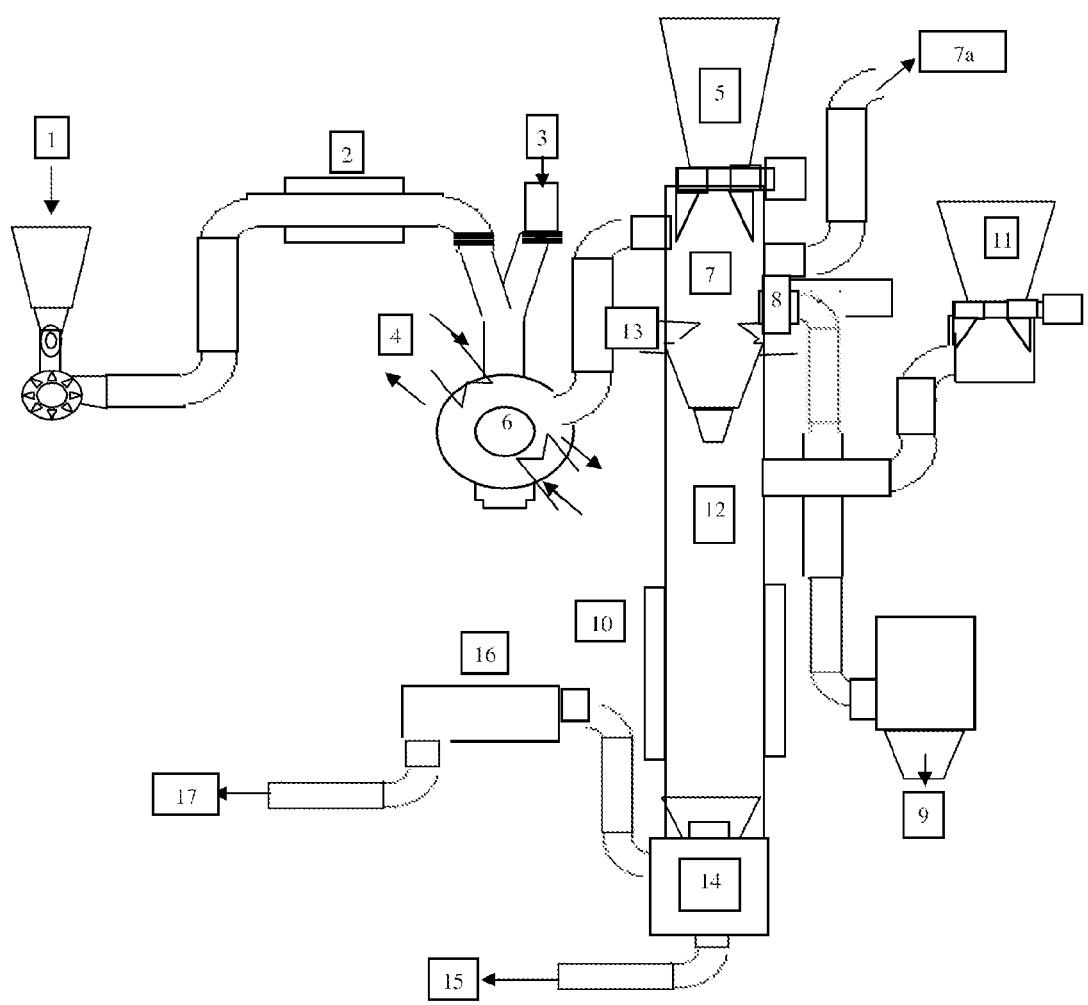
FIG. 1 is a simplified schematic view of the assembly for producing hydrogen gas and syngas in separate streams. Separate components of the assembly have been labeled 1-17.

Embodiments may involve a process of providing hydrogen gas and syngas in separate streams. The syngas maybe converted into synthetic crude. The invention involves a process where the hydrogen gas and syngas streams are not mixed. The hydrogen gas is produced from a metal/metal salt pair and water before the introduction of biomass feedstock into the assembly. Once the hydrogen has been channelled out of the assembly, the biomass feedstock is then introduced into the assembly leading to the production of syngas. Furthermore the present invention may involve a continuous process of providing hydrogen gas and syngas in separate streams. According to one embodiment, the hydrogen gas is produced from zinc sulphate, zinc and water.

The use of zinc catalyst to produce hydrogen gas may lead to the formation of zinc oxide. The zinc oxide may be directly reacted with biomass feedstock to produce zinc vapour, carbon monoxide and hydrogen. The zinc vapour may then be condensed before being re-introduced into the system as a zinc catalyst for hydrogen gas production. This may result in production of high purity hydrogen gas.

The formation of zinc oxide during hydrogen gas production and its subsequent conversion to zinc vapour in the presence of a biomass feedstock may be represented by the following equations:

$$Zn + ZnSO_4 + H_2O \rightarrow ZnO + H_2 + ZnSO_4 \qquad (i)$$

$$ZnO + \text{biomass feedstock} \rightarrow CO + Zn + H_2 \qquad (ii)$$

The production of hydrogen gas from zinc, zinc sulphate and water, shown by equation (i) may occur in a first stream. The hydrogen gas may be directed, without further purification, into a fuel cell to produce zero-carbon electricity. The production of carbon monoxide, hydrogen gas and zinc from the reaction between biomass feedstock and zinc oxide, shown by equation (ii), may occur in a second stream within the assembly. The biomass feedstock, in the absence of oxygen may dissociate into its basic components being hydrogen and carbon. The presence of embedded carbon may reduce the zinc oxide to zinc vapour and carbon monoxide. The carbon monoxide and hydrogen gas may then be hydrogenated to produce carbon neutral synthetic crude.

An embodiment provides a process wherein the reactions according to equations (i) and (ii) may occur in separate streams.

Referring to FIG. 1, a metal salt such as a zinc sulphate slurry is introduced into a hopper 1 before being pumped into a reactor 2. In particular, the zinc sulphate slurry may be a solid or a highly concentrated aqueous zinc sulphate solution. The zinc sulphate slurry is heated between 800-900° C. in the absence of oxygen in the reactor 2 causing the zinc sulphate to decompose into zinc oxide and sulphur trioxide. The decomposition of the zinc sulphate may be represented by the following equation:

$$ZnSO_4 \rightarrow ZnO + SO_3 \quad \text{(iii)}$$

The reactor 2 may comprise a heat source. The heat source may include but is not limited to a focused infrared heat, an atmospheric plasma reactor, a plasma torch, a molybdenum disilicate heating element or any combination thereof to produce a uniform temperature below 1000° C.

Water is then introduced into the system via an inlet 3 and mixed with the contents of the reactor 2 inside a vessel 6, to form sulphuric acid, represented by the equation below.

$$SO_3 + H_2O \rightarrow H_2SO_4 \quad \text{(iv)}$$

The temperature required for the decomposition of zinc sulphate is 800-900° C. whereas the temperature required for direct zinc hydrolysis is 1800° C.

The heat generated at vessel 6 is transferred away by way of heat exchanger 4 which is in fluid connection with the reactor 2.

The mixture from the vessel 6 is fed into a reaction chamber 7. A further metal, zinc, is also fed into the reaction chamber 7 via a hopper 5.

The sulphuric acid from vessel 6 then reacts with zinc, whilst heating at 800-850° C., to give zinc sulphate and hydrogen at a high rate of completion, as represented by the equation below:

$$Zn + H_2SO_4 \rightarrow ZnSO_4 + H_2 \quad \text{(v)}$$

The decomposition of the zinc sulphate also helps prevent the formation of a zinc oxide layer on the surface of the zinc particles, since the water in the system reacts with sulphur trioxide to form sulphuric acid and does not hydrolyse the zinc to afford zinc oxide. Therefore the formation of zinc oxide, from the reaction between zinc and water, is by-passed since the water is consumed with sulphur trioxide to form sulphuric acid.

The hydrogen gas is released from the system via an outlet 7a. Zinc sulphate catalyst is recovered at an outlet 9 from the reaction chamber 7 via a pipe 8. In particular, the zinc sulphate may be recovered from the reaction chamber 7 using a crystallizer at the outlet 9. In particular, the zinc fed into the reaction chamber 7 via the hopper 5 may have a particle diameter of 5 mm or less.

The metal, may include, but is not limited to zinc and/or iron in combination with a metal salt as catalyst. For example a zinc/zinc sulphate pair, zinc/zinc chloride pair, zinc/zinc nitrate pair, iron/iron sulphate pair etc. Other metal pairs also may be applicable, however any metal above Aluminium is not applicable. For example any metal of the reactivity series from Aluminium to Lead may be applicable, such as Aluminium, Titanium, Manganese, Zinc, Chromium, Iron, Cadmium, Cobalt, Nickel, Tin and Lead.

The sulphuric acid may be replaced with other acids such as hydrochloric acid or nitric acid. In these cases a different metal salt would be used accordingly. Zinc chloride would be used for hydrochloric acid and zinc nitrate would be used for nitric acid.

The zinc oxide produced in the reactor 2, which has passed through vessel 6 and reaction chamber 7, is then mixed with biomass feedstock fed into a vessel 12 via a hopper 11. The vessel 12 may be heated by way of a heat exchanger 13 where heat may be derived from the waste heat generated at the vessel 6.

The biomass feedstock may include, but is not limited to, agricultural wastes, crop residues, mill wood wastes, urban wood wastes, urban organic wastes, wood, wood residues, logging residues, trees, shrubs, sawdust, bark, short rotation woody crops, herbaceous woody crops, grasses, starch crops, sugar crops, forage crops, oilseed crops, algae, water weed, water hyacinth, reed and rushes.

The heated mixture from the vessel 12 then enters a reaction chamber 10.

The reaction chamber 10 is maintained at a temperature of at least 1200° C. The reaction chamber 10 may comprise a heat source. The heat source may include but is not limited to a focused infrared heat, an atmospheric plasma reactor, a plasma torch, a molybdenum disilicate heating element or any combination thereof to produce a uniform temperature of 1200° C. or more.

The reaction of zinc oxide and biomass feedstock at the reaction chamber 10 is slightly exothermic and produces a mixture comprising gaseous zinc vapour, carbon monoxide and hydrogen gas. The heat generated at reaction chamber 10 may also be recovered by way of a heat exchanger.

The gaseous mixture of zinc vapour, carbon monoxide and hydrogen gas is then passed through a condenser 14 wherein zinc vapour is condensed to form zinc and the resultant zinc is collected at an outlet 15. The zinc from the outlet 15 may be recycled and re-introduced at the hopper 5.

The in-situ formation of the zinc and zinc sulphate increases the efficiency (zinc and zinc sulphate formed in-situ can be re-used) of the process. The condensation of zinc vapour to produce zinc may take place at a different location so that space saving can be achieved where this is critical. The remote recovery of zinc may also be performed by removing and transporting the zinc oxide to a remote location before reducing the zinc oxide to form zinc.

The resultant syn-gas (carbon monoxide and hydrogen mixture) from the condenser 14 is fed into a hydrogenator 16 to produce synthetic crude which is collected at an outlet 17. The hydrogenation of syn-gas to produce synthetic crude may include, but it not limited to, a Fischer Tropsch process wherein a cobalt catalyst is used at low temperature and low pressure.

The apparatus illustrated in FIG. 1 allows for hydrogen gas to be fed directly to a fuel cell without further purification since the system produces high purity hydrogen gas in a separate stream from syngas. The apparatus allows for the direct channelling of high purity hydrogen gas away from the reactor system by comprising two separate reaction streams. The first reaction stream relates to features 1-9 of FIG. 1 where high purity hydrogen gas is produced and channelled away from the system at the outlet 7a. The second reaction stream relates to features 10-17 of FIG. 1 where zinc oxide produced from the first reaction stream is mixed with biomass feedstock leading to the recovery of zinc and the production of synthetic crude.

The invention claimed is:

1. A process of producing hydrogen gas and syngas in separate streams, the process comprising:
   a) decomposing a metal salt at a relatively low temperature to form an acid and a metal oxide;
   b) reacting the acid with a metal to form hydrogen gas and the metal salt;
   c) extracting the hydrogen gas from the product of step (b);
   d) heating the metal oxide with a biomass feedstock to produce a mixture comprising syngas and a metal vapour; and
   e) hydrogenating the syngas to produce synthetic crude, wherein the metal salt comprises at least one metal selected from the group consisting of aluminium, titanium, manganese, zinc, chromium, iron, cadmium, cobalt, nickel, tin and lead.

2. The process according to claim 1, wherein the metal and/or metal salt is zinc, zinc sulphate, or a combination thereof.

3. The process according to claim 1, further comprising condensing the metal vapour to obtain the metal, thereby separating the syngas and metal vapour.

4. The process according to claim 3, wherein the metal and metal salt are reused in a continuous process.

5. The method according to claim 1, wherein the acid is sulphuric acid, hydrochloric acid or nitric acid.

6. The method according to claim 1, wherein the relatively low temperature is less than 1000° C.

7. The method according to claim 1, wherein water is added to the decomposed metal salt to form the acid.

* * * * *